United States Patent [19]
Kosasky

[11] Patent Number: 5,788,649
[45] Date of Patent: *Aug. 4, 1998

[54] PRODUCT FOR USE IN THE MEASUREMENT OF VISCOELASTICITY AS A FUNCTION OF FEMALE OVULATION TIME

[76] Inventor: Harold J. Kosasky, 25 Boylston St., Chestnut Hill, Mass. 02167

[*] Notice: The term of this patent shall not extend beyond the expiration date of Pat. No. 5,640,968.

[21] Appl. No.: 555,124

[22] Filed: Nov. 8, 1995

Related U.S. Application Data

[63] Continuation-in-part of Ser. No. 524,741, Sep. 7, 1995, Pat. No. 5,640,968.
[51] Int. Cl.$^6$ .............. A61B 5/00; A61B 10/00; B65D 33/00
[52] U.S. Cl. .............. 600/551; 600/300; 600/304; 600/574; 600/33
[58] Field of Search .................. 128/738, 630, 128/760; 600/300, 304, 551, 574, 33

[56] References Cited

U.S. PATENT DOCUMENTS

| | | | |
|---|---|---|---|
| 3,982,423 | 9/1976 | Schuster | 73/54 |
| 4,002,056 | 1/1977 | Kapito et al. | 73/53 |
| 4,072,045 | 2/1978 | Kapito | 73/54 |
| 4,167,110 | 9/1979 | Kopito et al. | |
| 4,237,725 | 12/1980 | Kopito et al. | |
| 4,628,941 | 12/1986 | Kosasky | 128/759 |
| 4,779,627 | 10/1988 | Kosasky | 128/738 |
| 5,640,968 | 6/1997 | Kosasky | 128/738 |

OTHER PUBLICATIONS

Gerald Oster et al., "Cyclic Variation of Sialic Acid Content in Saliva", *American Journal of Obstetrics and Gynecology*, vol. 114, No. 2, Sep. 15, 1972, pp. 190–193.

L.E. Kapito et al., "The Tackiness Rheometer Determination of Viscoelasticity of Cervical Mucus," *Human Ovulation*, Elsevier/North–Holland Biomedical Press, 1979, pp. 351–361.

*Primary Examiner*—Aaron J. Lewis
*Assistant Examiner*—Dinh Nguyen
*Attorney, Agent, or Firm*—Morse & Altman

[57] ABSTRACT

A pair of components for an instrument for determining the female fertile period by measuring the viscoelasticity of saliva that includes a pair of strata composed of a rigid material, preferably glass or a polymer, and a surface on each strata, where the surface has a random distribution of peaks and valleys, the average depth from the peaks to the valleys is in the range of from about 10 picometers to about 100 micrometers, and the total area of the valley walls below one half of the average depth is from 35% to 65% of the total area of the surface. Preferably, the average depth of the valleys is in the range of 50 micrometers to 80 micrometers and the total area of the valleys below one half of the average depth is between 45% and 55% of the total area of the surface.

16 Claims, 5 Drawing Sheets

PRODUCT FOR USE IN THE MEASUREMENT OF VISCOELASTICITY AS A FUNCTION OF FEMALE OVULATION TIME

RELATED APPLICATION

This application is a continuation-in-part of application Ser. No. 08/524,741 entitled INSTRUMENT FOR MEASURING SALIVA VISCOELASTICITY TO DETERMINE FEMALE OVULATION TIME, filed on Sep. 7, 1995, in the name of Harold J. Kosasky, now U.S. Pat. No. 5,640,968.

GOVERNMENT FUNDING

The research involved in this application was funded in part by the National Institutes for Health, grant number 1 R41 HD32218-01. The intellectual property rights of the applicant and the government of the United States of America are governed by Title 37 Code of Federal Regulations Part 401.

BACKGROUND OF THE INVENTION

1. Field of the Invention

The present invention relates to the measurement of the viscoelasticity of saliva, and more particularly, to surfaces to which a saliva sample adheres for measuring its viscoelasticity in order to determine a woman's fertile period and ovulation time.

2. The Prior Art

It has been known that the cervical mucus of a female has a maximum fluidity just before ovulation, where ovulation is defined as the moment that an ovum is released from the follicle. This knowledge lead to the applicant's previous activities in the development of techniques for monitoring the viscoelasticity, or tackiness, and other properties of cervical mucus as a predictor of time of ovulation and fertile period and to improvements in rheometer or viscometer apparatus for measuring such viscoelastic properties. See, for example, L. E. Kopita and H. J. Kosasky, "The Tackiness Rheometer Determination of the Viscoelasticity of Cervical Mucus," *Human Ovulation*, edited by E. S. E. Hafez, Elsevier, North-Holland Biomedical Press, 1979, pp. 351 et seq., and U.S. Pat. Nos. 4,002,056 and 4,167,110. Though the viscoelasticity of the cervical mucus has several small dips in its characteristic curve of viscosity versus time preceding, during, and following ovulation (a four-day period), there is a distinct identifiable minimum viscoelasticity. Instruments designed to measure this effect are described in, for example, U.S. Pat. Nos. 4,002,056 and 4,072,045.

Saliva is now known to undergo physiochemical changes during the menstrual cycle, including a change in its viscoelasticity. Especially pronounced is the change in the viscoelasticity of sublingual saliva, the fluid excreted by the sublingual salivary gland located under the tongue. See, for example, S. S. Davis, "Saliva is Viscoelastic", Experientia, 26:1298, (1970), and R. H. Davis et al., "Saliva Viscosity Reflects the Time of Ovulation", Experientia, 30:911, (1974). As described in U.S. Pat. No. 4,779,627, issued on Oct. 25, 1988 to the present applicant, and entitled PROCESS AND APPARATUS FOR DETERMINING FEMALE OVULATION TIME BY MEASUREMENT OF SALIVA VISCOELASTICITY, incorporated herein by reference, the applicant previously discovered that sublingual saliva has a unique and reliably measurable minimum in viscoelasticity that is coincident with the ovulation cycle and its surge of estradiol.

There are devices on the market for measuring viscoelasticity to determine the female fertile period, but these devices are designed to use cervical mucus as a sample medium, rather than saliva. The viscoelasticity of cervical mucus is several orders of magnitude higher than that of saliva. So, devices designed to use cervical mucus as a sample medium are typically not sensitive enough to use saliva as a sample.

The devices for measuring viscoelasticity typically use two opposing surfaces to hold the sample, whether the sample is one of saliva or cervical mucus. The sample is placed between the surfaces, which have a known area, then the surfaces are moved to within a predetermined distance of each other. The actual measurement takes one of two forms. Either the surfaces are separated in a predetermined amount of time and the amount of force necessary to cause the sample to fracture is measured, or the surfaces are separated with a predetermined amount of force and the amount of time it takes for the sample to fracture is measured. In either case, the measurement is used to determine the sample's viscoelasticity.

The force of adhesion of the sample to the surfaces must be greater than the force of cohesion of the sample (the amount of force needed to fracture the sample), otherwise the sample will break away from the surface before it fractures, invalidating the measurement. In the prior art devices, because adhesion is a function of surface area but cohesion is not, the adhesion is made greater than the cohesion by enlarging the area of the opposing surfaces until the adhesion is greater. The problem is that the surface must be made so large that it cannot be used in a portable instrument.

Thus, there continues to be a need for a saliva sample surface that can be made small enough to fit in a portable instrument for measuring the viscoelasticity of sublingual saliva for the determination of female ovulation time.

SUMMARY OF THE INVENTION

The present invention comprises a pair of components for an instrument for determining the female fertile period by measuring the viscoelasticity of saliva. The components each include a stratum composed of a rigid material and having a surface which has a random distribution of peaks and valleys. The preferred average depth from the top of the peaks to bottom of the valleys is in the range of from about 10 picometers to about 100 micrometers and the most preferred average depth is in the range of 50 micrometers to 80 micrometers. The preferred total area of the valley walls below one half of the average depth is from 35% to 65% of the total area of the surface and the most preferred total area of the valleys is between 45% and 55% of the total area of the surface.

Preferably, the stratum is composed of glass or a polymer. If the stratum is glass, the surface is ground and if the stratum is a polymer, the surface is molded.

Preferably, the saliva has a viscoelasticity in the range of from 1 centipoise to 100 centipoise and the force of adhesion of the saliva to the surface is greater than the force of cohesion of the saliva.

BRIEF DESCRIPTION OF THE DRAWINGS

For a fuller understanding of the nature and object of the present invention, reference is made to the accompanying drawings, wherein.

DETAILED DESCRIPTION

The components of the present invention are used to hold sublingual saliva samples in instruments for measuring the viscoelasticity of sublingual saliva in order to determine the fertile period of a human female. The components can be used in a variety of designs of such instruments.

Measuring Viscoelasticity

Figure 1:
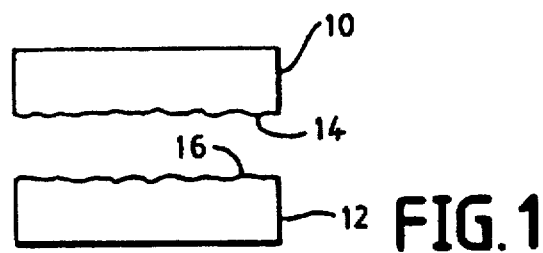
FIG. 1 is a front elevational view of two plates embodying the present invention.
Figure 2:
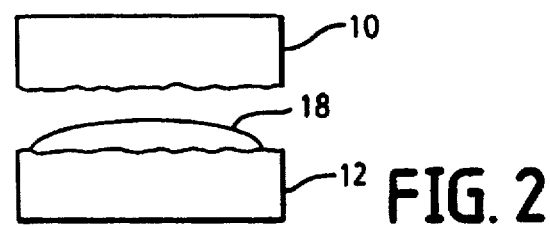
FIG. 2 is a front elevational view of the plates of FIG. 1 with a saliva sample.
Figure 3:
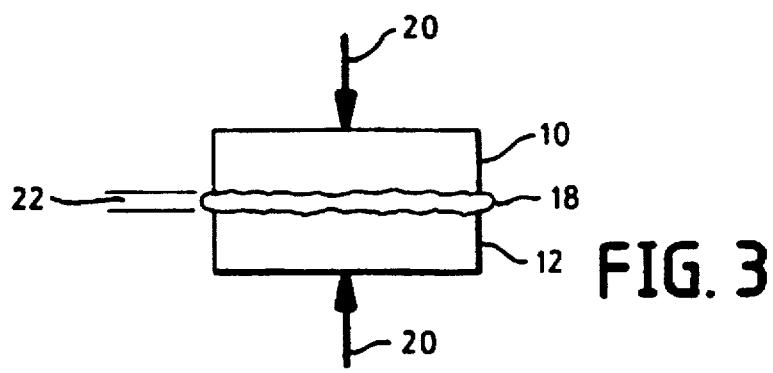
FIG. 3 is a front elevational view of the plates of FIG. 1 pressed together.
Figure 4:
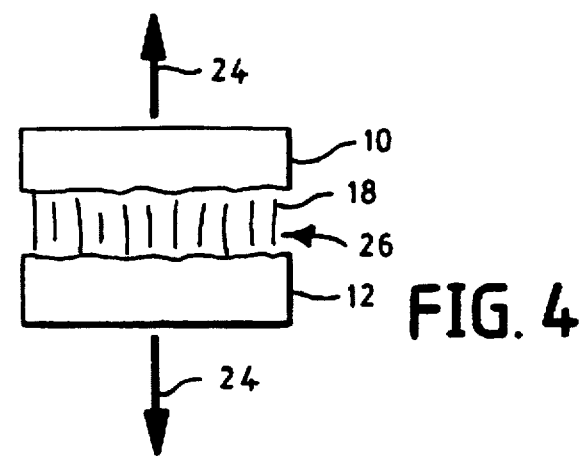
FIG. 4 is a front elevational view of the plates of FIG. 1 separating after pressure is released.

FIGS. 1 to 4 show the process by which the viscoelasticity of saliva is measured. In FIG. 1, a pair of plates 10, 12 having sample surfaces 14, 16 are spaced apart. In FIG. 2, a saliva sample 18 is placed between the sample surfaces 14, 16. Typically, the saliva sample is taken from the saliva pool under the tongue, the majority of which is sublingual saliva, mixed with a small amount of submandibular saliva. In FIG. 3, the plates 10, 12 are pressed together with a predetermined force 20 until the sample surfaces 14, 16 are a predetermined distance apart 22. The predetermined distance 22 must be small enough so that the saliva sample 18 coats the entire area of the sample surfaces 14, 16, but large enough so that the saliva sample 18 is not squeezed out from between the sample surfaces 14, 16. In FIG. 4, the plates 10, 12 are pulled apart by a separation force 24 until the saliva sample fractures, as at 26. Fracturing occurs when the cohesion of the saliva sample 18 is overcome, where cohesion is defined as the tendency of parts of a body of like composition to hold together. The action represented by FIG. 4 implies two ways of measuring: (1) using a predetermined separation force 24 and measuring the time it takes for the saliva sample 18 to fracture, or using a predetermined separation time and measuring the amount of separation force 24 needed to fracture the saliva sample 18.

The viscosity of a saliva sample 18 is a function of the separation force 24, the area of one of the sample surfaces 14, 16, and the amount of time that it takes for the sample surfaces 14, 16 to separate. These values are related by the following equation:

$$\text{viscosity} = \frac{\text{separation force/surface area}}{\text{separation rate}}$$

wherein the viscosity is calculated in poise (P), the separation force is measured in dynes (dy), the surface area is measured in square centimeters (cm$^2$), and the separation rate is measured in 1/seconds (s$^{-1}$). The separation force/surface area is also called the shear stress and the separation rate is also called the shear rate.

Note that the equation is one for viscosity, rather than for viscoelasticity. When using a Newtonian fluid, such as water, the equation will calculate pure viscosity. However, saliva is a non-Newtonian fluid. In a non-Newtonian fluid, there is an element of elastic recoil, or elasticity, along with the viscosity. Elasticity affects the separation time and separation force 24 of the plates 10, 12. Thus, the measurements used in the above equation are affected by the elasticity of the saliva sample 18. Because there is no specific equation for viscoelasticity, the equation for viscosity is used, and the viscoelasticity is measured in viscosity-equivalent units, giving a Newtonian equivalent of the combination of viscosity and elasticity found in the non-Newtonian saliva sample 18.

The portions of the calculated viscoelasticity attributed to the viscosity and to the elasticity depend upon the thickness of the saliva (density, not breadth). As the thickness increases, the portion attributed to viscosity increases as a percentage of the viscoelasticity. For example, in a very thick fluid, the proportion of viscosity to elasticity may be 80% to 20%, while in a very thin fluid, the proportion may be 20% to 80%.

Another factor to consider is that, not only do the proportions of viscosity and elasticity change as a fluid thickens, but the absolute values of the viscosity and elasticity also changes. For example, a thick fluid may have 80% of its viscoelasticity attributed to viscosity and 20% attributed to elasticity with absolute numbers of 64 poise attributed to viscosity and 16 poise attributed to elasticity, and a thin fluid may have 20% of its viscoelasticity attributed to viscosity and 80% attributed to elasticity with absolute numbers of 5 poise attributed to viscosity and 20 poise attributed to elasticity.

Adhesion of a Saliva Sample to the Surface

The use to which the present invention is put is in an instrument for measuring the viscoelasticity of a saliva sample 18, and this measurement relies on the adhesion of the saliva sample 18 to the sample surfaces 14, 16, where adhesion is defined as the tendency, due to intermolecular forces, for matter to cling to other matter. In order to have a valid measurement, the force of adhesion of the saliva sample 18 to the sample surfaces 14, 16 must be greater than the force of cohesion of the saliva sample 18 so that the saliva sample 18 fractures before it separates from one of the sample surfaces 14, 16. Therefore, sample surfaces 14, 16 having a force of adhesion for the saliva sample 18 that is greater than the force of cohesion of the same saliva sample 18 must be provided.

The adhesion of the saliva sample 18 to a sample surface 14, 16 occurs over the entire area over which the saliva sample 18 and sample surface 14, 16 make contact. So, the larger the contact area, the proportionally greater will be the adhesion of the saliva sample 18 to the sample surfaces 14, 16.

The viscosity portion of the viscoelasticity measurement also increases in proportion to the amount of contact surface area, but because the viscosity is only part of the viscoelasticity measurement, the viscoelasticity only increases by an amount equal to the percentage that the viscosity is of the viscoelasticity. So, there is a point in the increase in surface area where the adhesion and cohesion forces are equal and any additional increase in surface area results in a greater adhesion than cohesion.

One way to increase the area of the sample surface 14, 16 is to increase the outer dimensions of the sample surface 14, 16. Another way is to roughen the surface, so that there are a plurality of valleys extending into the plates 10, 12. The contact area includes the area covered by the walls of any valleys extending into the sample surface 14, 16 to which the saliva sample can come into contact. Roughening the sample surfaces 14, 16 provides a greater contact area without increasing the outer profile of the plates 10, 12. This is a critical characteristic of the present invention. The size of the instrument is no longer substantially dependent upon the size of the plates 10, 12, and can be made small enough, for example, to fit into a breast pocket.

The Preferred Surface

Figure 5:
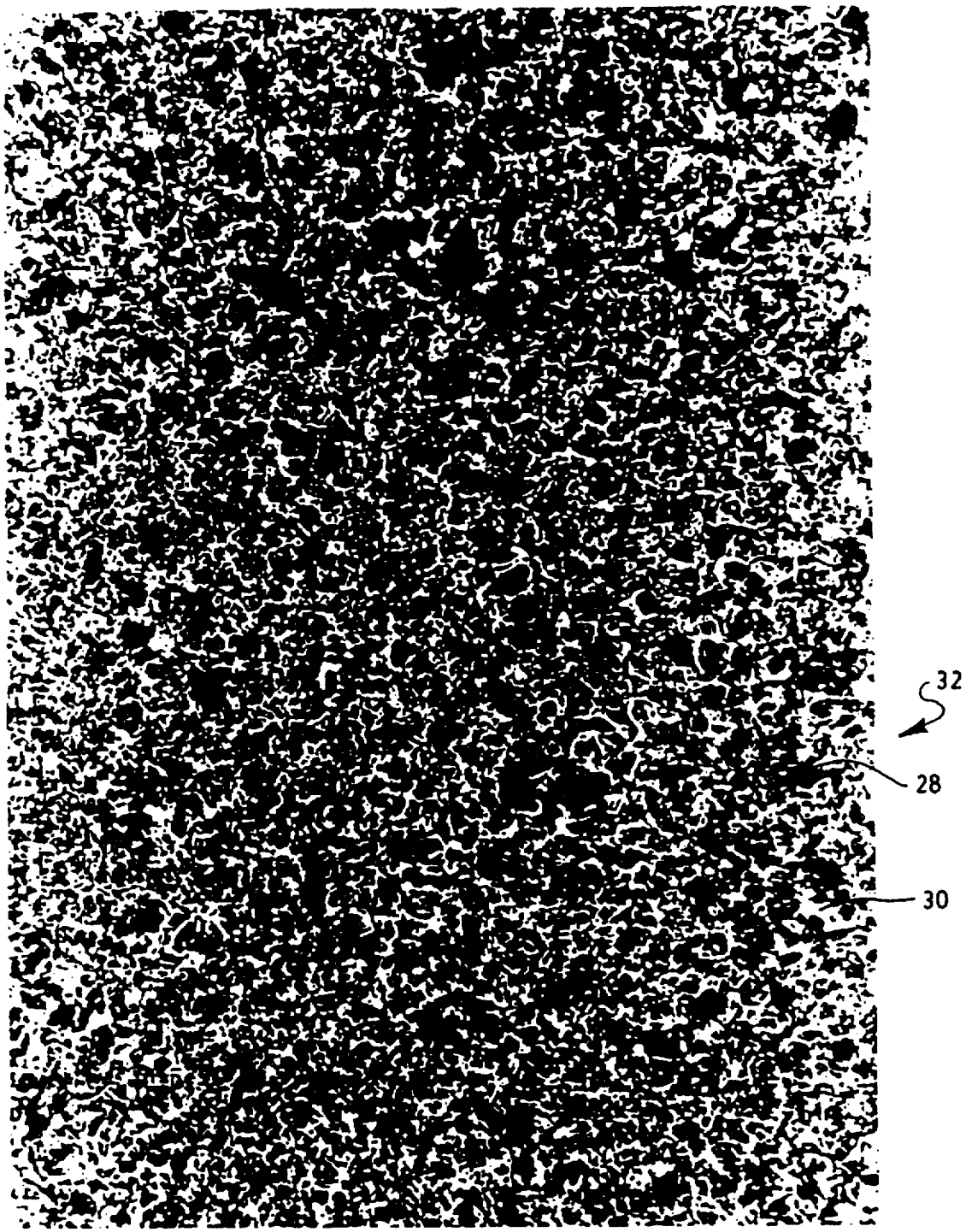
FIG. 5 is a low-power microphotograph of a sample surface.
Figure 6:
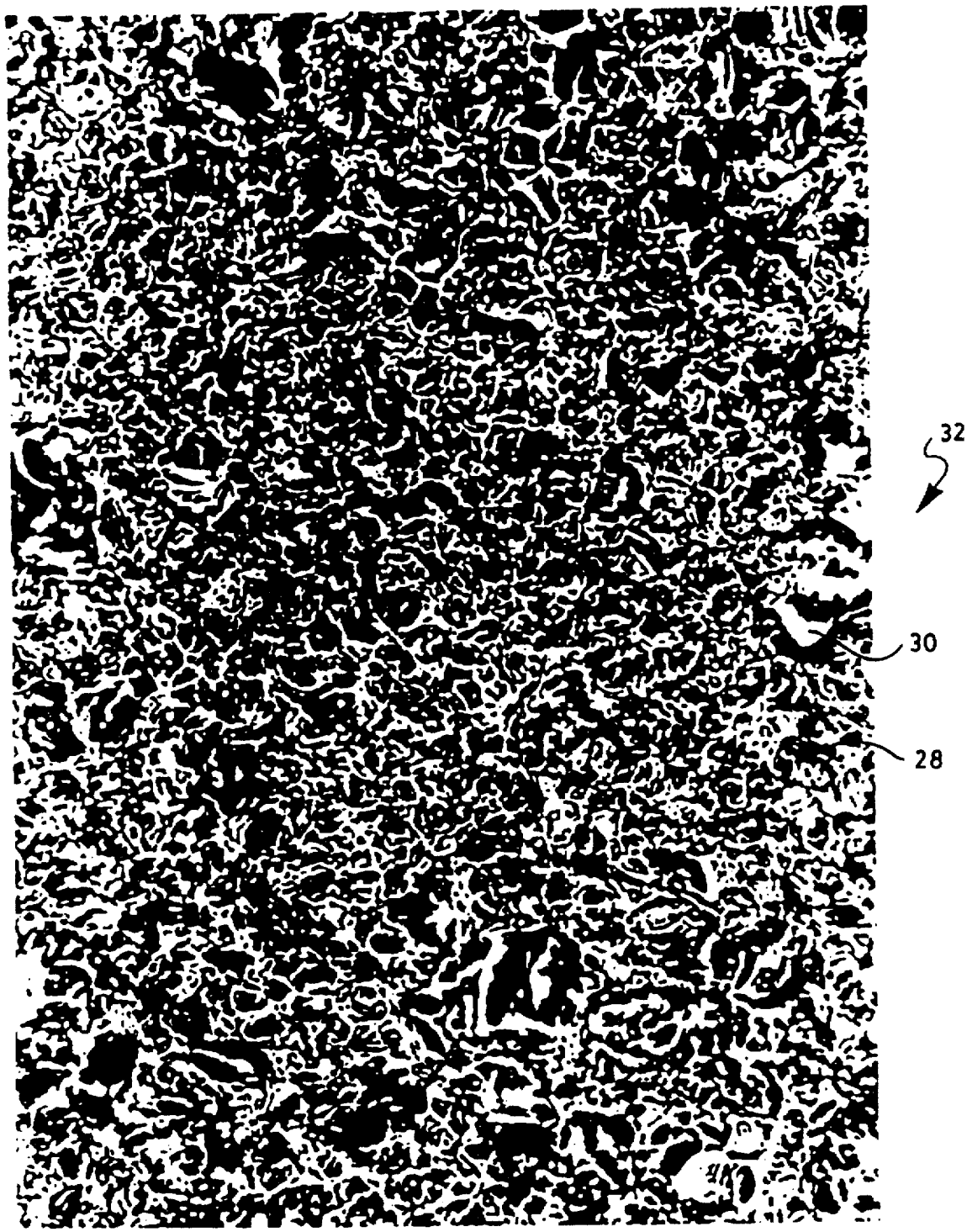
FIG. 6 is a high-power microphotograph of a sample surface.
Figure 7:
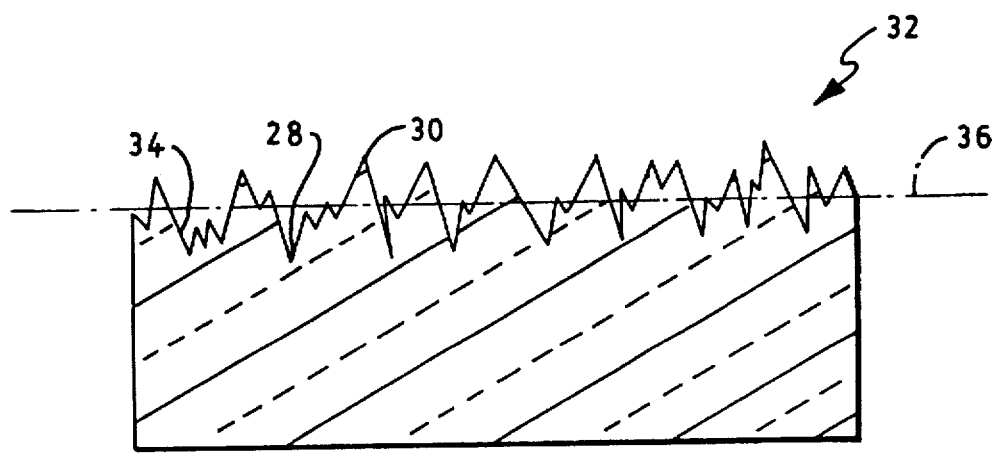
FIG. 7 is an enlarged cross-section of a portion of a plate.

FIG. 5 is a low-power (10×) microphotograph, FIG. 6 is a high-power (40×) microphotograph, and FIG. 7 is a greatly enlarge cross-section of a preferred roughened sample surface 32. As can be seen, the sample surface 32 is characterized by a random distribution of irregularly-shaped peaks 30 and valleys 28. There are two basic parameters that are important in characterizing the sample surface 32 when used in an instrument for measuring saliva viscoelasticity. The first of these parameters is the average depth of the valleys, as measured from the plane defined by the tops of the peaks 30. The preferred range of this average is from 10 picometers (pm) to 100 micrometers (μm), and the most preferred range is from 50 μm to 80 μm.

The second parameter is the amount of valley area 34, the sum of the surface area of the valley walls below one half of the average depth of the valleys 36, relative to the total surface area. The preferred range of valley area 34 is from 35% to 65% of the total surface area, and the most preferred range is from 45% to 55%.

The preferred amount of roughening will double the smooth size of the surface area. This is achieved by having an average depth of approximately 65 μm and a valley area of approximately 50%.

If the average depth of the valleys 28 is too shallow, such as less than 10 pm, the sample surface 32 will be too smooth and will not work adequately for two reasons. First, the area of the sample surfaces 32 will be so small that the saliva sample will not adhere with a force greater than the cohesion of the saliva sample. As explained above, if the force of adhesion is smaller than the force of cohesion of the saliva sample, the saliva sample will separate from the sample surfaces 32 before it fractures.

Second, one effect of very smooth surfaces of like material is that they will adhere to each other on a molecular level, requiring a very large separation force to pull the surfaces apart. The separation force would be too large to be practical in actual usage because sublingual saliva has a very low viscoelasticity, which requires a finely calibrated separation force for an accurate measurement. And because it is more difficult to calibrate a large force to the same absolute accuracy as a small force, the larger force needed to separate smooth surfaces would be more difficult to calibrate to a particular value than the small force needed to separate roughened surfaces, resulting in a less accurate measurement of viscosity.

If the average depth of the valleys 28 is too great, such as greater than 100 μm, or the ratio of valley area 34 to total area is too large, such as greater than 65%, the surface will also not work adequately because the saliva sample 18 would spread into the deep or large valleys 28, leaving the saliva sample 18 remaining outside the valleys 28 too small for an accurate measurement. If the saliva sample 18 is too small, it will not cover the entire area of the sample surfaces 14, 16, resulting in an inaccurate value for the fracturing surface area, and rendering the calculated viscoelasticity inaccurate.

If the ratio of valley area 34 to total area is too low, such as less than 35%, the sample surface 14, 16 will also not work adequately because the area of the sample surfaces 14, 16 will be so small that the saliva sample 18 will not adhere with a force greater than the cohesion of the saliva sample 18. As explained above, if the force of adhesion is smaller than the force of cohesion of the saliva sample 18, the saliva sample 18 will separate from the sample surfaces 14, 16 before it fractures.

Composition of the Surface

Preferably, the plates 10, 12 and, as a result, the sample surfaces 14, 16, are composed of either glass or a rigid plastic. If the surface is composed of glass, it must be ground to the desired roughness. The characteristics of the grit used to grind the glass must correspond to the characteristic desired for the surface.

A disadvantage of glass is that each surface is different from every other surface. The differences in the details of the ridges and valleys of each surface means that the surface area will differ slightly between each pair of surfaces. As a result, there will always be some uncertainty in the measurements relative to repeatability because the surface areas are not equal from measurement to measurement. However, in general, the uncertainty will be small enough that it is not significant in a series of measurements.

Plastics are molded rather than ground. A mold with particular surface characteristics etched into it can be created and used to form sample surfaces with consistent surface topology and size. The mold can be created using a previously ground glass surface as the pattern. Although no two molded surfaces can be exactly alike, the differences from one surface to the next will not be nearly as great as the difference from one ground surface to the next, resulting in better repeatability of the measurements.

Another advantage to using plastics for the sample surfaces is that the surfaces can be molded as an integral component of the instrument, rather than being produced separately and later attached to the instrument as would be necessary if glass were used.

Glass does have an advantage over plastic in that it is harder and will not scratch as easily as plastic. This disadvantage of plastic is a problem only if the sample surfaces are intended to be re-used. In actual instrument designs, however, the surfaces are not intended to be reused. The previous saliva sample will dry in the valleys, preventing the new saliva sample from adhering properly, and causing the measurement with the new saliva sample to be invalid.

Simple Instrument Embodying the Present Invention

Figure 8:
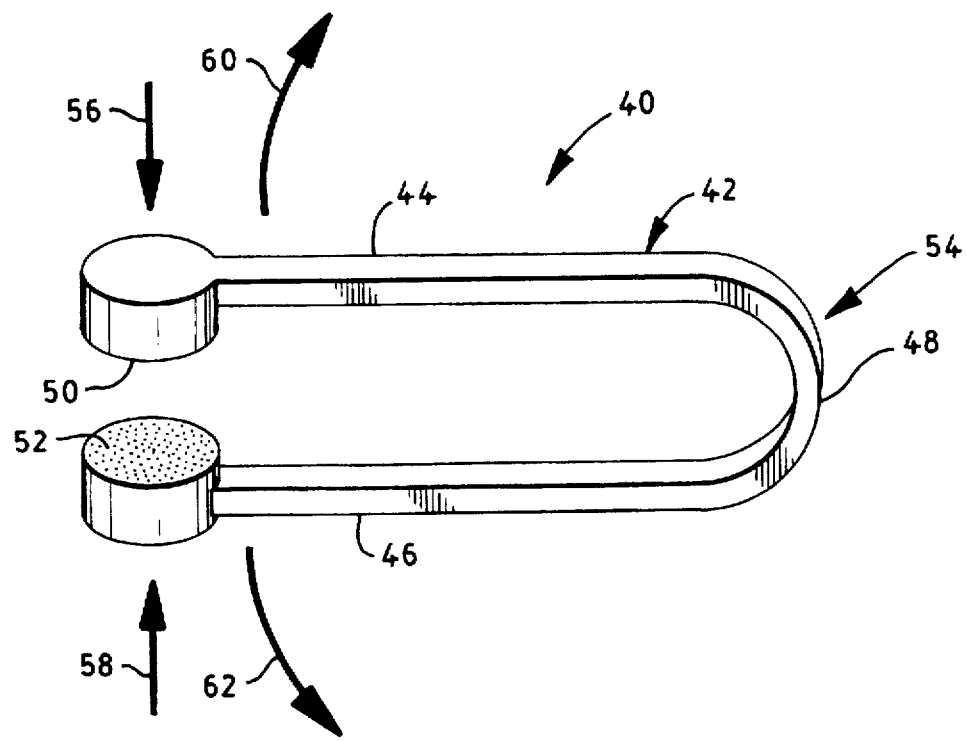
FIG. 8 is a perspective view of a simple instrument embodying the present invention.

A simple instrument 40 for measuring saliva viscoelasticity is shown in FIG. 8. It consists of a strip of flexible material 42 bent into a U shape so that there are two arms 44, 46 and a cross piece 48. The outer extremities of the arms 44, 46 have sample surfaces 50, 52. The sample surfaces 50, 52 are either integral with the strip 42 or are on plates (not shown) that are attached to the arms 44, 46. The cross piece of the strip 48 acts as a spring 54 between the arms 44, 46, biasing the sample surfaces 42, 44 apart, as at 60, 62.

To use the instrument 40, the sample surfaces 50, 52 are dipped into the saliva pool under the tongue to obtain a sample of mostly sublingual saliva. The saliva sample must be large enough to completely coat the sample surfaces 50, 52. The sample surfaces 50, 52 are then forced to within a predetermined distance by pressing either side of the arms 44, 46 with, for example, thumb and finger, as at 56, 58, at a predetermined pressure for a predetermined minimum period of time. This pressure and time forces the saliva sample to extrude to coat the sample surfaces 50, 52 uniformly and adhere to the sample surfaces 50, 52. After at least the predetermined minimum time, the pressure is released. The amount of time it takes for the spring 54 to cause the sample surfaces 50, 52 to separate is measured and used to determine the viscoelasticity of the saliva sample, as detailed above.

In a typical pocket-size instrument, the sample surfaces 50, 52 will be round with a diameter of about 0.5 cm, providing a nominal surface area of about 0.2 cm². However, in order for the force adhesion of the saliva sample to the sample surface 50, 52 to be greater than the force of cohesion of the saliva sample, the sample surfaces 50, 52 are roughened to an average depth of about 65 μm and a valley area of approximately 50%. This results in a contact area of twice the nominal surface area, namely about 0.4 cm².

Figure 9:
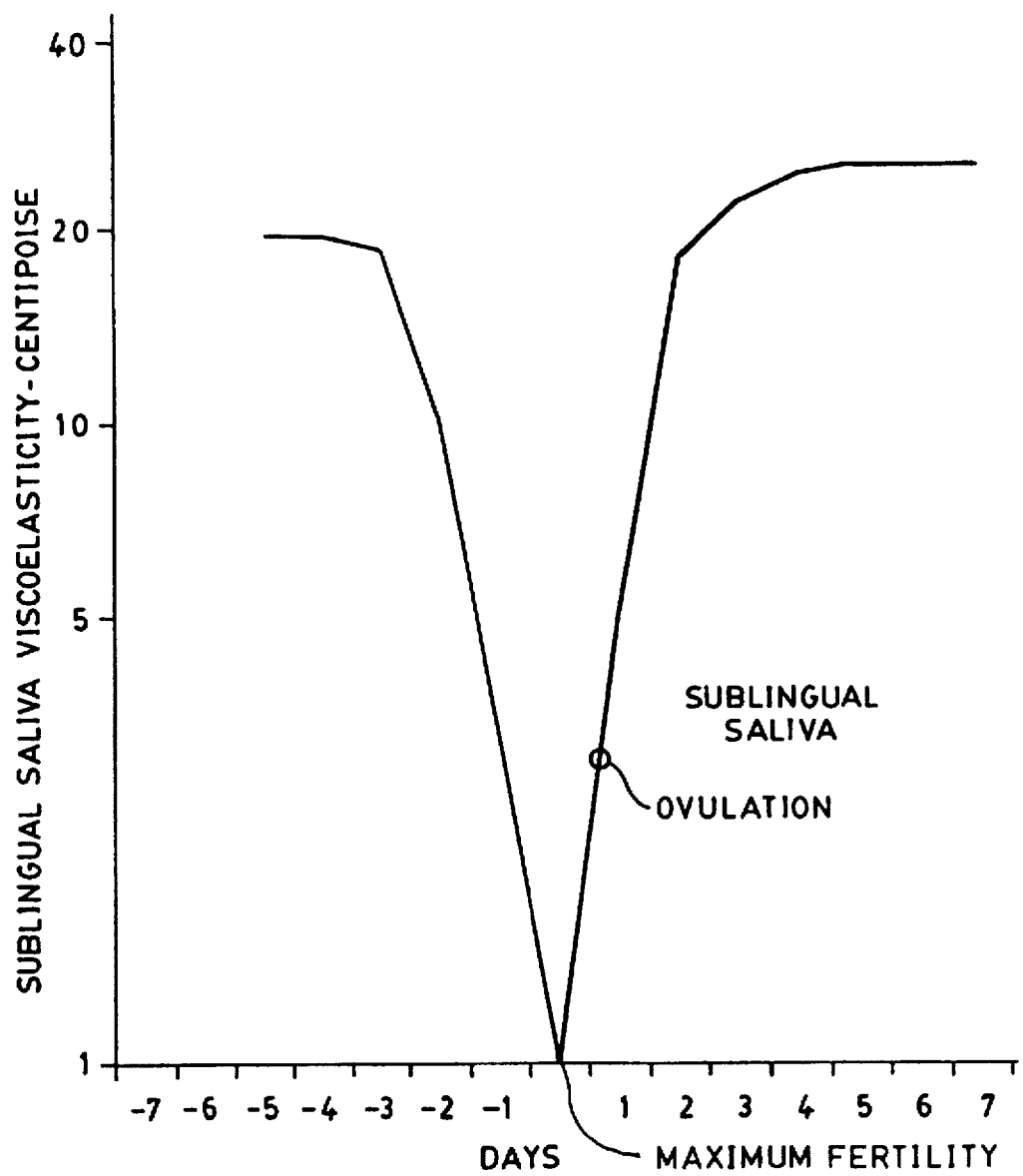
FIG. 9 is a curve showing the relationship between the viscoelasticity of sublingual saliva and ovulation time.

The curve of FIG. 9 shows how the viscoelasticity of sublingual saliva relates to the fertile period. The viscoelasticity falls over a period of from 2 to 4 days until about 16 to 24 hours prior to ovulation and then rises over a period of from 1 to 2 days. The trough of the curve, which is at the time of maximum fertility, has a viscoelasticity of about 0.01 P. In order to predict the fertile period, to account for variety among saliva samples from different people, and to make sure that the instrument does not separate too quickly or slowly, the instrument is calibrated to separate in about the preferred time of 30 seconds when the viscoelasticity of the saliva sample is about 0.03 P. To accommodate this requirement, the spring force 60, 62 is set to about 0.0004 dy, giving a shear stress/area of about 0.001 dy/cm². Thus, the equation for viscoelasticity (in viscosity-equivalent units of poise) for the instrument is $$viscoelasticity = 0.001 \; dy/cm^2 * T$$

wherein T is the separation time in seconds. This equation permits a practical range for the viscoelasticity of the saliva sample of from 0.001 to 0.10 P. A shear rate of 100 seconds results in a measurement of 0.1 P and a shear rate of 1 second results in a measurement of 0.001 P.

The values for separation force, time, and surface area in the above example are for illustration only. In an instrument designed for actual use, these values will vary depending on the physical details of the instrument. If the area of the sample surfaces is larger or smaller than in the example above, the separation force must be larger or smaller, respectively, if the separation time is to remain the same. The same is true of the surface area if the separation force must be different. In practical terms, the range of values for surface area, separation force, and separation time can vary widely, by as much as a factor of 100.

What is claimed is:

1. A component for an instrument for determining the female fertile period by measuring the viscoelasticity of saliva, said component comprising:
   (a) a stratum composed of a rigid material;
   (b) a surface on said stratum;
   (c) said surface having a random distribution of valleys, said valleys having walls;
   (d) the average depth of said valleys being in the range of from about 10 picometers to about 100 micrometers;
   (e) the total area of said valley walls below one half of said average depth being from 35% to 65% of the total area of said surface; and
   (f) wherein the majority of said saliva is a combination of sublingual and submandibular saliva.

2. The component of claim 1 wherein said average depth is in the range of 50 micrometers to 80 micrometers.

3. The component of claim 1 wherein said total area of said valleys below one half of said average depth is between 45% and 55% of the total area of said surface.

4. The component of claim 1 wherein said stratum is composed of glass.

5. The component of claim 4 wherein said surface is ground.

6. The component of claim 1 wherein said stratum is composed of a polymer.

7. The component of claim 6 wherein said surface is molded.

8. The component of claim 1 wherein said saliva has a viscoelasticity in the range of from 1 centipoise to 100 centipoise and the force of adhesion of said saliva to said surface is greater than the force of cohesion of said saliva.

9. A component for an instrument for determining the female fertile period by measuring the viscoelasticity of saliva, said component comprising:
   (a) a stratum composed of a rigid material;
   (b) a surface on said stratum;
   (c) said surface having a random distribution of valleys, said valleys having walls;
   (d) the average depth of said valleys being in the range of from about 50 micrometers to 80 micrometers;
   (e) the total area of said valley walls below one half of said average depth being from 45% and 55% of the total area of said surface; and
   (f) the majority of said saliva being sublingual saliva.

10. The component of claim 9 wherein said stratum is composed of glass and said surface is ground.

11. The component of claim 9 wherein said stratum is composed of a polymer and said surface is molded.

12. An instrument for determining the female fertile period by measuring the viscoelasticity of a saliva sample, said instrument comprising:
   (a) a pair of plates composed of a rigid material;
   (b) said plates having surfaces for contiguous registration with said saliva sample therebetween, said saliva sample being in contact with each of said surfaces;
   (c) a means for urging said surfaces to within a predetermined distance of each other;
   (d) a means for separating said surfaces from each other with a predetermined force;
   (e) said saliva sample having a viscoelasticity in the range of from 1 centipoise to 100 centipoise;
   (f) the size of the area of contact between said saliva sample and each of said surfaces being such that, when said urging means is applied, then said separating means is applied, the force of adhesion of said saliva sample to each of said surfaces is greater than the force of cohesion of said saliva sample; and
   (g) the majority of said saliva sample being sublingual saliva.

13. The instrument of claim 12 wherein said plates are composed of glass.

14. The instrument of claim 13 wherein said surfaces are formed by grinding.

15. The instrument of claim 12 wherein said plates are composed of a polymer.

16. The instrument of claim 15 wherein said surfaces are formed by molding.

* * * * *